(12) United States Patent
Kazama et al.

(10) Patent No.: US 9,168,010 B2
(45) Date of Patent: Oct. 27, 2015

(54) X-RAY IMAGING APPARATUS AND MEDICAL IMAGE PROCESSING APPARATUS

(71) Applicants: Kabushiki Kaisha Toshiba, Minato-ku (JP); Toshiba Medical Systems Corporation, Otawara-shi (JP)

(72) Inventors: Masahiro Kazama, Sakura (JP); Masakuni Fujise, Otawara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 190 days.

(21) Appl. No.: 13/900,240

(22) Filed: May 22, 2013

(65) Prior Publication Data

US 2013/0272500 A1 Oct. 17, 2013

Related U.S. Application Data

(63) Continuation-in-part of application No. PCT/JP2013/002376, filed on Apr. 5, 2013.

(30) Foreign Application Priority Data

Apr. 11, 2012 (JP) .................................. 2012-090315

(51) Int. Cl.
*A61B 6/10* (2006.01)
*A61B 6/03* (2006.01)
*A61B 6/00* (2006.01)

(52) U.S. Cl.
CPC . *A61B 6/10* (2013.01); *A61B 6/032* (2013.01); *A61B 6/482* (2013.01); *A61B 6/542* (2013.01)

(58) Field of Classification Search
CPC ....................................................... A61B 6/542
See application file for complete search history.

(56) References Cited

U.S. PATENT DOCUMENTS

| 4,797,905 | A | * | 1/1989 | Ochmann et al. | ............. 378/108 |
| 7,813,471 | B2 | | 10/2010 | Hirokawa et al. | |
| 8,189,740 | B2 | | 5/2012 | Tsukagoshi et al. | |

FOREIGN PATENT DOCUMENTS

| CN | 1427659 A | 7/2003 |
| CN | 1689523 A | 11/2005 |
| CN | 101385649 A | 3/2009 |

(Continued)

OTHER PUBLICATIONS

International Search Report issued on May 7, 2013 for PCT/JP2013/002376 filed on Apr. 5, 2013 with English Translation of Categories.

(Continued)

*Primary Examiner* — Hoon Song
(74) *Attorney, Agent, or Firm* — Oblon, McClelland, Maier & Neustadt, L.L.P.

(57) ABSTRACT

An X-ray imaging apparatus including: an imaging unit which includes an X-ray tube that emits an X-ray to a subject and an X-ray detector that is so disposed as to face the X-ray tube; an input unit which inputs a plurality of imaging conditions including a tube current and a tube voltage of the X-ray tube, and sets an imaging protocol of the imaging unit; and an image creation unit which calculates an exposed dose when at least the tube voltage or the tube current is varied, and creates an index image that is made by overlapping an image showing the exposed dose on a two-dimensional map that is represented by the tube voltage and the tube current.

9 Claims, 3 Drawing Sheets

(56) References Cited

FOREIGN PATENT DOCUMENTS

| CN | 101453952 A | 6/2009 |
|----|----|----|
| CN | 202066969 U | 12/2011 |
| CN | 202143287 U | 2/2012 |
| EP | 648466 | 9/1994 |
| JP | 8-196528 | 8/1996 |
| JP | 2003-010168 | 1/2003 |
| JP | 2009-66288 | 4/2009 |
| JP | 2010-172362 | 8/2010 |
| JP | 2010-264163 | 11/2010 |
| WO | 2007/138979 | 12/2007 |

OTHER PUBLICATIONS

International Written Opinion issued on May 7, 2013 for PCT/JP2013/002376 filed on Apr. 5, 2013.
Combined Office Action and Search Report issued Feb. 2, 2015 in Chinese Patent Application No. 201380000277.8 (with partial English language translation).

* cited by examiner

X-RAY IMAGING APPARATUS AND MEDICAL IMAGE PROCESSING APPARATUS

CROSS-REFERENCE TO RELATED APPLICATION

This application is a continuation of International Application No. PCT/JP2013/002376, filed on Apr. 5, 2013, which is based upon and claims the benefit of priority from the prior Japanese Patent application No. 2012-090315, filed on Apr. 11, 2012, the entire contents of which are incorporated herein by reference.

FIELD

Embodiments described herein relate to an X-ray imaging apparatus such as an X-ray CT apparatus that displays an image showing an exposed dose on a two-dimensional map of tube current and tube voltage of an X-ray tube. The embodiments also relate to a medical image processing apparatus.

BACKGROUND

Conventionally, as an X-ray imaging apparatus, for example, an X-ray computed tomography apparatus (X-ray CT apparatus) has been used. The X-ray CT apparatus is designed to collect measurement data by exposing a subject to an X-ray from an X-ray tube and using an X-ray detector to detect the X-ray that has passed through the subject. The X-ray CT apparatus is designed to rotate the X-ray tube and the X-ray detector, and reconstruct an image on the basis of collected data, which are obtained at each angle, thereby obtaining a CT image.

The X-ray CT apparatus sets the tube voltage and tube current of an X-ray tube, and collects data. However, if the tube voltage and the tube current remain fixed when data is collected by an imaging, the quality of the image varies depending on physical dimensions of the subject (such as body weight and body height). In order to increase the quality of the image, the tube voltage and the tube current are set to higher levels, or either the tube voltage or the tube current is modulated, during an imaging operation.

Moreover, an appropriate X-ray dosage varies according to regions of the subject whose imaging. For example, thick regions of the body, such as a head, thorax, and abdomen are irradiated with a high energy X-ray. Thinner areas Are irradiated with a low energy X-ray. In general, the tube voltage is set to a constant level, and the tube current is modulated, thereby ensuring the quality of an image of each region of the body. The X-ray CT apparatus may employ a dual energy scan. The dual energy scan is a process of imaging operation with the use of two or more types of X-ray energy at varying tube voltages when the images of the same area Are imaging, thereby obtaining an image of each level of energy.

Meanwhile, in the case where the tube current or the tube voltage is varied when imaging, a patient is exposed to a higher dose of radiation if the tube current or the tube voltage is increased, for example. Conventionally, in order to prevent the exposed dose from exceeding a specified value, CTDIvol or DLP is generally displayed on a console as an index of the exposed dose. CTDIVol (CT Dose Index Volume) represents the density of the X-ray, and DLP (Dose Length Product) represents the total dose and CTDIVol and DLP are index values that represent reference doses. The reference doses (CTDIvol, DLP) are set based on the body weight, body height, age, and other factors of a subject, for example.

However, the above displaying process is designed so far only to meet requirements of the IEC standards. There is an example in which the change of exposed dose is numerically displayed. However, in the process of providing numerical information, it is difficult to represent the change of exposed dose of a complex imaging protocol such as tube current modulation (or tube voltage modulation) or dual energy scan.

DETAILED DESCRIPTION

An X-ray imaging apparatus of an embodiment includes an imaging unit which includes an X-ray tube that emits an X-ray to a subject and an X-ray detector that is so disposed as to face the X-ray tube; an input unit which inputs a plurality of imaging conditions including a tube current and tube voltage of the X-ray tube, and sets an imaging protocol of the imaging unit; and an image creation unit which calculates an exposed dose when at least the tube voltage or the tube current is varied, and creates an index image that is made by overlapping an image showing the exposed dose on a two-dimensional map that is represented by the tube voltage and the tube current.

Hereinafter, the X-ray imaging apparatus of an embodiment will be described in detail with reference to the accompanying drawings. Incidentally, the same portions in each diagram are represented by the same reference symbols.

FIRST EMBODIMENT

Figure 1:
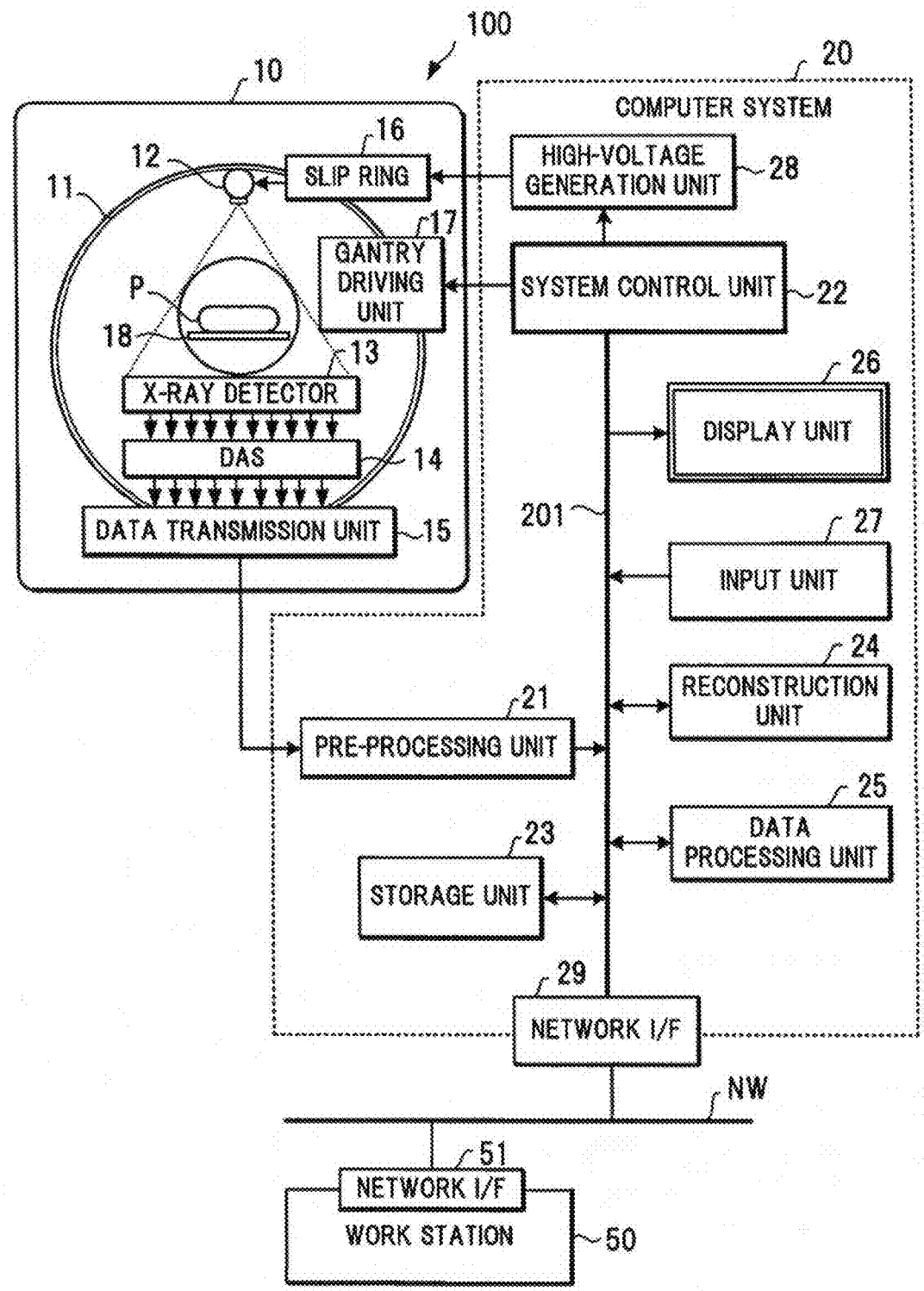
FIG. 1 is a block diagram showing the configuration of an X-ray imaging apparatus according to an embodiment.

FIG. 1 is a block diagram showing the configuration of the X-ray imaging apparatus according to the embodiment, showing an X-ray CT apparatus as an example. The X-ray CT apparatus 100 includes a gantry 10 and a computer system 20. The gantry 10 is designed to collect projection data pertaining to a subject P, and includes a rotation frame 11, an X-ray tube 12, an X-ray detector 13, a data collection unit 14, a non-contact data transmission unit 15, a slip ring 16, and a gantry driving unit 17.

The rotation frame 11 is a ring that is rotationally driven, and is equipped with the X-ray tube 12 and the X-ray detector 13. There is an opening in a central portion of the rotation frame 11. Into the opening, the subject P that is placed on a top plate 18 of a bed (not shown) is inserted.

The X-ray tube 12 is a vacuum tube that generates an X-ray. To the X-ray tube 12, a power required to emit an X-ray (the tube current and the tube voltage) is supplied from a high-voltage generation unit 28 (described later) via the slip ring 16. The X-ray tube 12 uses a supplied high voltage to accelerate electrons in such a way that the electrons collide with a target, thereby emitting an X-ray to the subject P that is placed within an effective visual field region.

The X-ray detector 13 is designed to detect the X-ray that has passed through the subject P. The X-ray detector 13 is attached to the rotation frame 11 so as to face the X-ray tube 12. For example, the X-ray detector 13 is a detector of a multi-slice type includes a plurality of detection elements which are made by combining scintillators and photodiodes are arranged in a two-dimensional pattern. The X-ray tube 12 and the X-ray detector 13 constitute an imaging unit.

The data collection unit 14 is called DAS (Data Acquisition System). The data collection unit 14 converts a signal that is output for each channel from the X-ray detector 13 into a voltage signal, and amplifies the voltage signal, and converting the voltage signal to a digital data. The digital data is transmitted to the computer system 20 via the non-contact data transmission unit 15.

The gantry driving unit 17 rotationally drives the rotation frame 11. As the rotation frame 11 is driven rotationally, the X-ray tube 12 and the X-ray detector 13 rotate around an axis that is substantially identical to a body axis of the subject P in such a way that the X-ray tube 12 and the X-ray detector 13 face each other. If the top plate 18 is moved along the body axis direction of the subject P during the rotation, a so-called helical scan can be performed in a way that scans the subject in a spiral manner.

The computer system 20 includes a pre-processing unit 21, a system control unit 22, a storage unit 23, a reconstruction unit 24, a data processing unit 25, a display unit 26, an input unit 27, and the high-voltage generation unit 28. The computer system 20 also includes a bus line 201 and a network interface (I/F) 29. The network interface 29 is connected to a network NW such as LAN (Local Area Network). As a result, information acquired by the X-ray CT apparatus 100 can be output to external apparatus such as a PC (Personal Computer) and a workstation 50 which constitutes a medical image processing apparatus, and information coming from the external apparatus can be input into the X-ray CT apparatus 100.

The pre-processing unit 21 receives raw data from the data collection unit 14 via the non-contact data transmission unit 15, and carries out sensitivity correction and X-ray intensity correction. The system control unit 22 is connected to the bus line 201, and totally controls the X-ray CT apparatus 100. The system control unit 22 performs a scan process, a signal process, an image creation process, an image display process, and other processes.

The raw data that have been corrected in various ways by the pre-processing unit 21 are referred to as "projection data." The data are temporarily stored in the storage unit 23 via the bus line 201. The reconstruction unit 24 is equipped with a plurality of reconstruction methods. The reconstruction unit 24 is designed to reconstruct image data according to the reconstruction method specified by an operator.

The data processing unit 25 performs an image process, such as window conversion or RGB processing, on the reconstruct image data generated by the reconstruction unit 24 in order to display the data. The data processing unit 25 then outputs the data to the display unit 26. Moreover, on the basis of an instruction from the operator, the data processing unit 25 generates a tomographic image of an arbitrary cross section, a projection image from an arbitrary direction, a three-dimensional image, and other images, and outputs the images to the display unit 26. The storage unit 23 stores image data such as tomographic image data that have been reconstructed, as well as the raw data.

The display unit 26 displays a CT image such as a computed tomography image that is input from the data processing unit 25. The display unit 26 also displays an exposed dose on a tube voltage-tube current two-dimensional map (which will be detailed in FIG. 2 and subsequent diagrams). The input unit 27 includes a keyboard, various switches, mouse, and the like, and allows an operator to set the tube voltage and tube current of the X-ray tube and the like, as well as to input various scan conditions and the like. The high-voltage generation unit 28 supplies the power required to emit the X-ray to the X-ray tube 12 via the slip ring 16.

The system control unit 22 sets an imaging protocol on the basis of conditions such as the tube voltage and the tube current, which are input from the input unit 27. During a scan process, on the basis of the set imaging protocol, the system control unit 22 controls the high-voltage generation unit 28. The system control unit 22 also controls the gantry driving unit 17 and the top plate 18 to control a feed amount and speed of the subject in the body-axis direction, a rotation speed and pitch of the X-ray tube 12 and X-ray detector 13, an X-ray emission timing, and the like. As a result, a data collection (scan) process of an X-ray CT image can be performed.

Incidentally, if the tube voltage and the tube current are set, for example, a reference value that is preset according to the body weight, body height, age, and other factors is stored in a storage unit based on the reference value, the tube voltage and the tube current are input depending on physical dimensions of an actual patient, and an imaging protocol is set. The tube voltage and the tube current may be set depending on a to-be-examined region. In this case, appropriate-quality images of a thorax, internal organs, and other parts can be collected.

Furthermore, when the tube voltage and the tube current are set as the input unit 27 is operated, the system control unit 22 calculates an exposed dose on the basis of the set value. Moreover, the system control unit 22 creates an index image showing the calculated exposed dose, and displays the created the index image on a display screen of the display unit 26. The index image is made by overlapping an image showing the exposed dose on a two-dimensional map that is represented by the tube voltage and the tube current. Accordingly, the system control unit 22 constitutes an image creation unit that calculates an exposed dose when at least the tube voltage or the tube current is varied, and creates the index image that is made by overlapping the image showing the exposed dose on the two-dimensional map that is represented by the tube voltage and the tube current.

Figure 2:
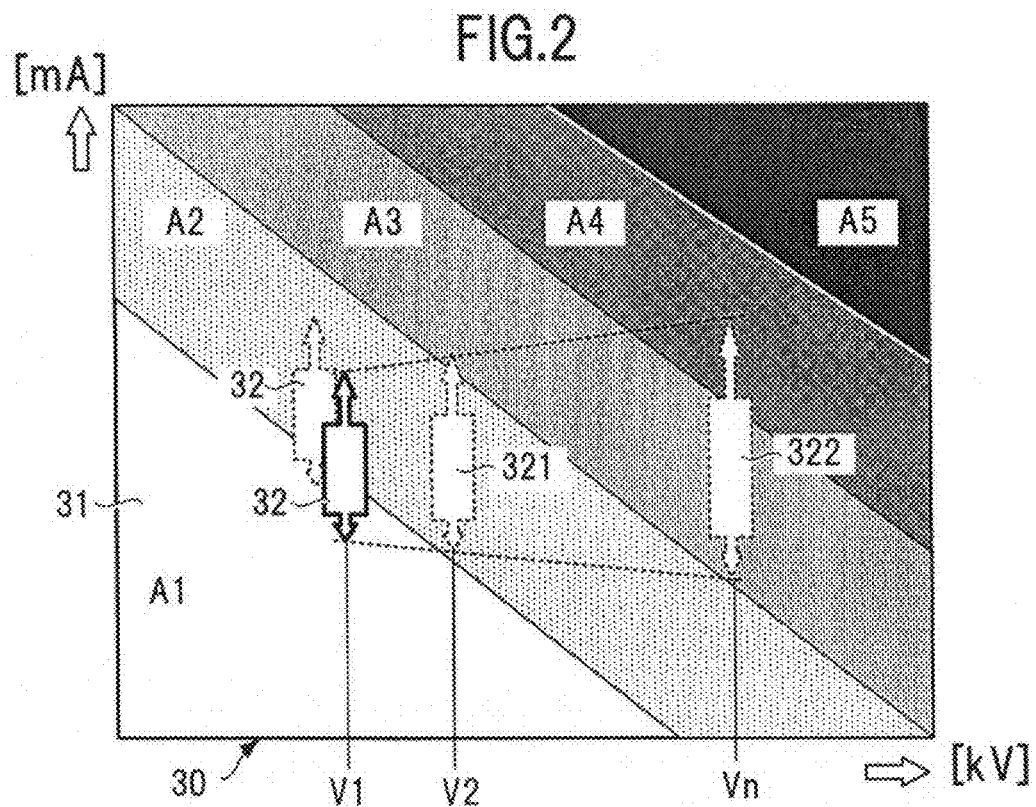
FIG. 2 is an explanatory diagram showing one example of an index image that is displayed on a display unit according to the embodiment.

FIG. 2 is an explanatory diagram showing one example of the index image that is displayed on the display unit 26. In FIG. 2, an index image 30 includes a two-dimensional map 31, and an image 32 shows an exposed dose which is overlapped on the two-dimensional map 31 and The two-dimensional map 31 is made up of the vertical axis which represents the tube current [mA], and the horizontal axis which represents the tube voltage [kV]. The two-dimensional map 31 is divided into a plurality of areas A1, A2, . . . , and A5, which are defined by the tube current and the tube voltage. The areas A1, A2, . . . , and A5 are displayed in different colors. For example, the area A1 where both the tube current and the tube voltage are low is displayed in blue. The areas A2 to A5 where the tube current and the tube voltage become higher are displayed in colors close to red. Incidentally, shown in FIG. 2 is an example in which the two-dimensional map 31 is divided into the five areas A1 to A5. However, the two-dimensional map 31 may be divided into more than five areas, or fewer than five areas The position and size on the two-dimensional map 31 of the image 32 that shows the exposed dose vary depending on the tube current and tube voltage set by the input unit 27. For example, in the tube current modulation in which the tube voltage is set to a constant level (e.g. V1) and the tube current is varied, the image 32 that shows the exposed dose is displayed as an image that extends in a vertical-axis direction. Normally, the tube current modulation is often used to the imaging of each portion. Therefore, in response to a change in tube current, the image 32 that shows the exposed dose is changed in the vertical-axis direction. Moreover, as the tube voltage is set to a higher level, the exposed dose increases when the tube current is changed. Therefore, as the tube voltage is set to a higher level (indicated by V2 and Vn, for example), images 321 and 322 showing an exposed dose become larger.

Figure 3A:
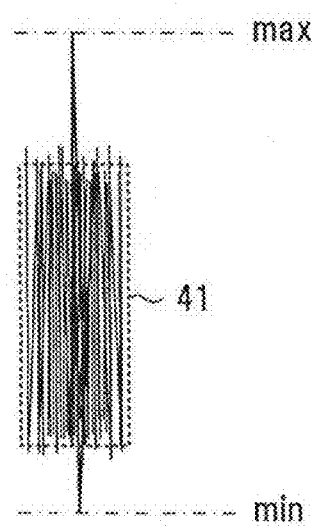
FIGS. 3A and 3B are explanatory diagrams showing an example of creating the index image according to the embodiment.
Figure 3B:
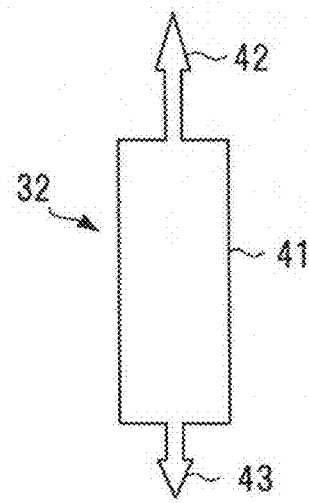

FIGS. 3A and 3B are explanatory diagrams showing an example of creating the index image 30. For example, as shown in FIG. 3A, the exposed dose is usually within an average amount and predetermined distribution indicated by a dotted-line frame 41. However, in some cases, the exposed dose may instantaneously become larger or smaller, or reach peak values (max, min). Accordingly, an average exposed dose and a maximum-minimum range (max-min) are acquired in advance for each imaging protocol so that, when a conditions for the tube current and tube voltage are input, the image 32 showing a corresponding exposed dose can be created.

On the image 32 showing the exposed dose, as shown in FIG. 3B, the average level and the distribution are indicated by a frame 41, and the peak values (max, min) are schematically summarized with arrows 42 and 43 before being displayed. As a result, when the tube current or the tube voltage is varied, the average exposed dose, the maximum value, and the minimum value can be displayed.

In this case, on the two-dimensional map 31, a critical area where both the tube current and the tube voltage are high and the exposed dose is over an acceptable value is represented by A5, and a area that comes just before the critical area is represented by A4. If the image 32 showing the exposed dose is displayed in the area A4 or A5, a warning, such as a blinking the image 32 may be displayed. As a result, an examiner (operator) is able to set the tube current and the tube voltage again, and correct the tube current and the tube voltage in such a way that the image 32 showing the exposed dose will be displayed in any area other than the critical area A5 (or A4), or in the areas A1 to A3 for example.

Figure 4:
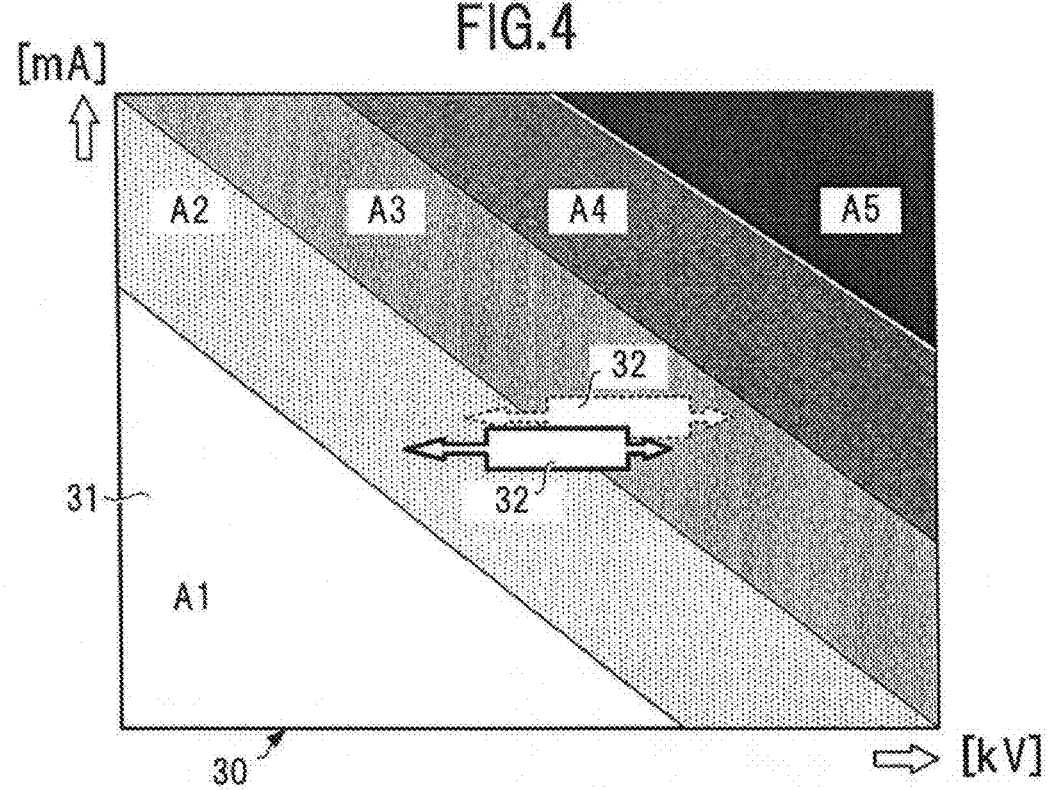
FIG. 4 is an explanatory diagram showing another example of displaying the index image according to one embodiment.

FIG. 4 is an explanatory diagram showing another example of displaying the index image 30. FIG. 4 is made by overlapping the image 32 which shows an exposed dose on a tube voltage-tube current two-dimensional map 31, in case of the tube voltage modulation in which the tube current is set to a constant level while the tube voltage is varied. In the case of FIG. 4, the image 32 showing the exposed dose is displayed as an image that is extended in a horizontal-axis direction as the tube voltage is varied. In general, in most cases, the tube voltage remains constant and the tube current is varied. However, in some cases, the tube voltage is varied when an X-ray is emitted. Therefore, the above displaying operation is also effective.

Figure 5:
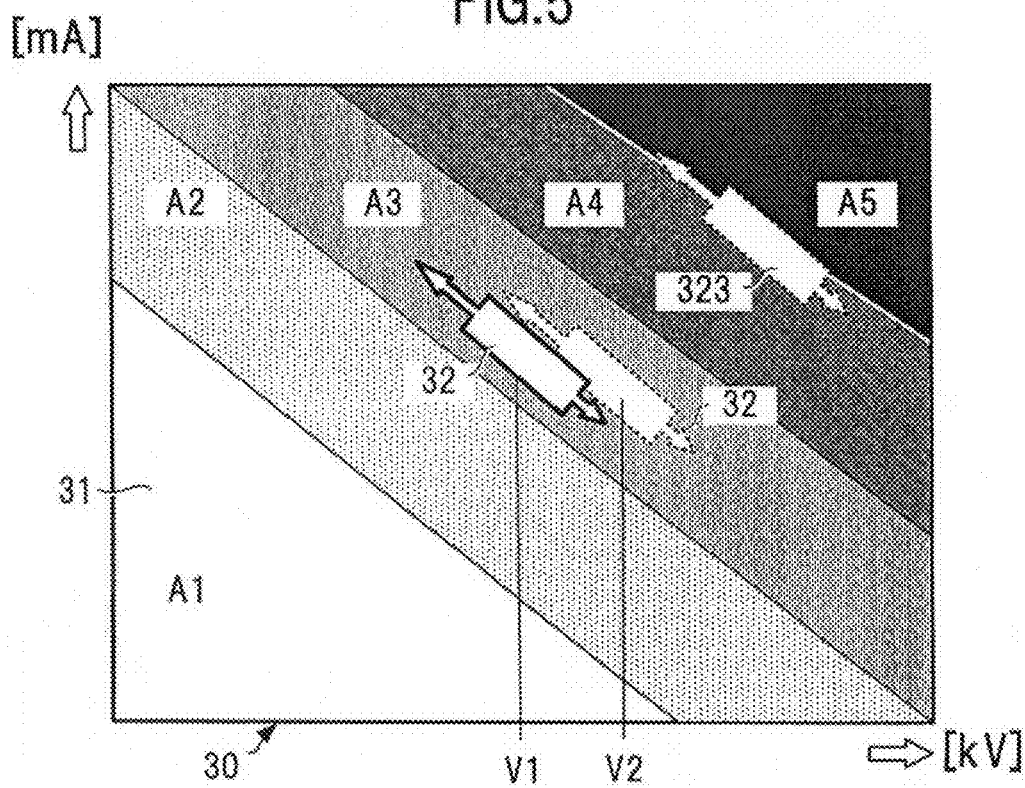
FIG. 5 is an explanatory diagram showing still another example of displaying the index image according to one embodiment.

FIG. 5 is an explanatory diagram showing still another example of displaying the index image 30. In an example of FIG. 5 is shown the image 32 which shows an exposed dose when both the tube current and the tube voltage are varied. In general, in most cases, the tube voltage remains constant while the tube current is varied. However, when a dual energy scan is carried out, the displaying described in FIG. 5 is suitable. The image 32 showing the exposed dose is displayed as an image that extends in an oblique direction with respect to the horizontal and vertical axes so as to correspond to the tube current and the tube voltage.

In the dual energy scan, a same region of the subject are imaging with the use of X-ray energy of a high tube voltage and X-ray energy of a low tube voltage as the tube current is varied. Two X-ray image data sets that are obtained by using X-rays of different radiation qualities are used to carry out a diagnosis. Accordingly, if both the tube current and the tube voltage are varied when the imaging, the image 32 showing the exposed dose such as that shown in FIG. 5 is displayed, the tube current and the tube voltage are so set that the image 32 is outside the critical area (e.g. the area A5 or A4).

In that manner, the index image 30 that contains the image 32 showing the exposed dose can be displayed. Therefore, when an imaging plan is made, an imaging protocol can be so set as to bring about an appropriate exposed dose. Moreover, even when the imaging is actually, the image 32 showing the exposed dose can be displayed in real time. Therefore, if the image 32 is approaching the critical area, a warning can be displayed to an examiner (operator) to urge the examiner (operator) to reset. FIG. 5 shows the situation where an image 323 showing an exposed dose has entered the critical areas A4 and A5. A warning image 323 is displayed so as to blink, or is displayed in different colors, for example.

As described above, the image 32 showing the exposed dose is displayed on the tube current-tube voltage two-dimensional map. Moreover, the position of the image displayed or the size of the image is changed according to the tube current and the tube voltage. Therefore, compared with the case where numbers are simply displayed, the examiner can be intuitively notified of which level the exposed dose is at. Therefore, it is possible to visually figure out whether the exposed dose is within an acceptable area or a critical area.

FIGS. 2, 4, and 5 show the examples in which the image showing the exposed dose is displayed in the case of the following imaging protocols the tube current modulation, the tube voltage modulation, and the dual energy. All the protocols are complex involving a variation in exposed dose during the imaging operation. Therefore, the exposed dose is visually indicated as a maximum-minimum range, or as a statistical distribution, thereby making it easier to visually figure out a variation in exposed dose in the protocol.

According to the above-described embodiment, it is possible to visually display a variation in exposed dose depending on an imaging protocol, and to carry out visually.

Incidentally, according to the above embodiment, the X-ray CT apparatus is described as an example. However, the present embodiment can be applied to any apparatus that contains an X-ray tube and an X-ray detector. For example, the present embodiment can be applied to an X-ray imaging apparatus called an angiographic apparatus, in which an X-ray tube and an X-ray detector are fixed to a C-shaped arm (C-arm), and the C-arm is moved in a body-axis direction of a subject placed on a top plate of a bed, or rotated around the body axis of the subject in order to an imaging of the subject from different angular directions.

Moreover, described in the above embodiment is the example in which the index image 30 is displayed on the display unit 26 of the X-ray CT apparatus 100. However, the index image 30 may be displayed on a workstation 50 which is a medical image processing apparatus. In this case, for example, the workstation 50 includes functional processing units that are similar to the system control unit 22, storage unit 23, data processing unit 25, display unit 26, and other units of the computer system 20.

As shown in FIG. 1, the workstation 50 includes a network interface 51 connected to a network NW. The workstation 50 is able to acquire the information acquired by the X-ray CT apparatus 100 via the network interface 51. That is, the network interface 51 constitutes an acquisition unit that acquires the imaging conditions including the tube current and tube voltage of the X-ray tube 12 on the basis of an imaging protocol that is set in the imaging unit that includes the X-ray tube 12 and the X-ray detector 13.

The workstation 50 is designed to process an image acquired by the X-ray CT apparatus 100, and display an arbitrary image. In the workstation 50, functional processing units that are similar to those of the computer system 20 are formed. Therefore, the workstation 50 can acquire various kinds of information from the X-ray CT apparatus 100 via the network NW, and can calculate an exposed dose on the basis of the conditions for the tube voltage and the tube current, which are set in the X-ray CT apparatus 100. Based on the calculated exposed dose, on a display screen of the workstation 50, the index image 30 such as the one shown in FIG. 2, 4, or 5, can be displayed.

A system control unit inside the work station 50 constitutes an image creation unit that calculates an exposed dose when at least the tube voltage or tube current of the X-ray CT apparatus 100 is varied, and creates the index image 30 that is made by overlapping the image 32 showing an exposed dose on a two-dimensional map 31 that is represented by the tube voltage and the tube current.

The index image 30 includes the image 32 showing an exposed dose as shown in FIGS. 2, 4, and 5. Therefore, a doctor or the like can look at the index image 30 that is displayed on the display screen of the work station 50, and closely watch the image 32 showing the exposed dose. For example, the doctor can instructs to the examiner (operator) who operates the X-ray CT apparatus 100, an appropriate tube current or tube voltage.

Moreover, described above is the example in which a plurality of areas A1, A2, . . . , and An, which are defined by the tube current and the tube voltage on the two-dimensional map, are distinguished and displayed in different colors. However, the areas may be displayed in colors of the same color systems but in different shades of color. For example, the critical area A5 may be displayed in dark red, and the area A1 in light red. A plurality of areas A1, A2, . . . , and An may be displayed with the use of contour lines, or by gradations. The image 32 showing the exposed dose is not limited to those shown in the diagrams, and may be displayed in different shapes.

While certain embodiments have been described, these embodiments have been presented by way of example only, and are not intended to limit the scope of the invention. Indeed, the novel apparatus described herein may be embodied in a variety of other forms; furthermore, various omissions, substitutions and changes in the form of the apparatus described herein may be made without departing from the spirit of the inventions. The accompanying claims and their equivalents are intended to cover such forms or modifications as would fall within the scope and spirit of the inventions.

What is claimed is:

1. An X-ray imaging apparatus comprising:
an imaging unit which includes an X-ray tube that emits an X-ray to a subject and an X-ray detector that is so disposed as to face the X-ray tube;
an input unit which inputs a plurality of imaging conditions including a tube current and tube voltage of the X-ray tube, and sets an imaging protocol of the imaging unit;
an image creation unit which calculates an exposed dose when at least the tube voltage or the tube current is varied, and creates an index image that is made by overlapping an image showing the exposed dose depending on a setting values of the tube current and tube voltage on a two-dimensional map that is represented by the tube voltage and the tube current; and
a display unit which displays the index image created by the image creation unit.

2. The X-ray imaging apparatus according to claim 1, wherein
the image creation unit changes the position and size of the image showing the exposed dose that is displayed on the two-dimensional map in accordance with setting values of the tube current and tube voltage.

3. The X-ray imaging apparatus according to claim 1, wherein
the image creation unit creates, as the image showing the exposed dose, an image showing an average level, maximum value, and minimum value of the exposed dose corresponding to the tube current and tube voltage.

4. The X-ray imaging apparatus according to claim 1, wherein
the image creation unit divides the two-dimensional map into a plurality of areas in response to an increase in the tube current and tube voltage.

5. The X-ray imaging apparatus according to claim 4, wherein
the image creation unit displays a warning when the image showing the exposed dose is displayed in a preset area of the two-dimensional map that is divided into a plurality of areas.

6. The X-ray imaging apparatus according to claim 4, wherein
the image creation unit distinguishes the plurality of areas of the two-dimensional map by different colors.

7. The X-ray imaging apparatus according to claim 1, wherein
the image creation unit creates the index image when an imaging plan is made, and creates the index image when a real time imaging on the basis of the imaging protocol.

8. A medical image processing apparatus comprising:
an acquisition unit which acquires a plurality of imaging conditions including a tube current and tube voltage of an X-ray tube, on the basis of an imaging protocol that is set in an imaging unit including the X-ray tube that emits an X-ray and an X-ray detector that is so disposed as to face the X-ray tube;
an image creation unit which calculates an exposed dose when at least the tube voltage or the tube current is varied, and creates an index image that is made by overlapping an image showing the exposed dose depending on a setting values of the tube current and tube voltage on a two-dimensional map that is represented by the tube voltage and the tube current; and
a display unit which displays the index image created by the image creation unit.

9. The medical image processing apparatus according to claim 8, wherein
the image creation unit changes the position and size of the image showing the exposed dose that is displayed on the two-dimensional map in accordance with setting values of the tube current and tube voltage.

* * * * *